United States Patent [19]

Schanzlin

[11] Patent Number: 4,664,110

[45] Date of Patent: May 12, 1987

[54] CONTROLLED RATE FREEZING FOR CRYOREFRACTIVE SURGERY

[75] Inventor: David J. Schanzlin, San Marino, Calif.

[73] Assignee: University of Southern California, Los Angeles, Calif.

[21] Appl. No.: 713,220

[22] Filed: Mar. 18, 1985

[51] Int. Cl.$^4$ ............................................. A61F 17/36
[52] U.S. Cl. .................................................. 128/303.1
[58] Field of Search ..................................... 128/303.1

[56] References Cited

U.S. PATENT DOCUMENTS 4,483,341 11/1984 Witteles .......................... 128/303.1

OTHER PUBLICATIONS

John May, "Sub-Zero Cell Storage," *Animal Tissue Culture: Advances in Technique*, Ed. Wasley Williams & Wilkins, Baltimore, 1973.
Frank M. Polack, MD, et al., "Incorporation of Sodium Sulfate S 35 by Cryopreserved Corneal Grafts in Vivo," *Arch Ophthal*, 81, pp. 577–582, Apr. 1969.
Joseph A. Capella, M.S., et al. *Corneal Preservation: Clinical and Laboratory Evaluation of Current Methods*, Charles C. Thomas, Springfield, Ill., pp. 287–293, 1965.
Perry S. Binder, M.D., et al., "Refractive Keratoplasty," *Arch Ophthalmol*, 101, pp. 1591–1596, 1983.
David J. Schanzlin, M.D., et al., "Cryolathe Corneal Injury," *Cornea*, 2, pp. 57–68, 1983.
M. H. Friedlander, M.D., "Keratophakia Using Preserved Lenticules," *Ophthamology*, 87, No. 7, pp. 687–692, Jul. 1980.
Richard C. Troutman, M.D., et al., "Keratophakia: A Preliminary Evaluation," *Ophth AAO*, 86, pp. 523–530, Apr. 1979.
James V. Aquavella, M.D., et al., "Morphological Variations in Corneal Endothelium Following Keratophakia and Keratomileusis," *Ophthamology*, 88, No. 8, pp. 721–723, Aug. 1981.
Theodore P. Werblin, M.D., et al., "Epikeratophakia: The Surgical Correction of Aphakia," *Arch Ophthamol*, 99, pp. 1957–1960, Nov. 1981.
Larry F. Rich, M.D., et al., "Keratocyte Survival in Keratophakia Lenticules," *Arch Ophthalmol*, 99, pp. 677–680, Apr. 1981.
Frederick A. Jakobiec, M.D., et al., "Keratophakia and Keratomileusis—Comparison of Pathologic Features in Penetrating Keratoplasty Specimens," *Ophthalmology*, 88, No. 12, pp. 1251–1259.
Perry S. Binder, M.D., et al., "The Histopathology of a Case of Keratophakia," Clinicopathologic Case Reports, *Arch Ophthalmol*, 100, pp. 101–105, Jan. 1982.
José I. Barraquer, M.D., "Keratomileusis for Myopia and Aphakia," *Ophthalmology*, 88, No. 8, pp. 701–708, Aug. 1981.
Casimir A. Swinger, M.D., et al., "Keratophakia and Keratomileusis—Clinical Results," *Ophthalmology*, pp. 709–715, Aug. 1981.
José Ignacio Barraquer, *Queratomileusis y Queratofaquia*, Instituto Barraquer de America, Bogota, Columbia, pp. 200–203, 1980.
Richard A. Villasenor, M.D., "Refractive Keratoplasty Instruction Manual," Doheny Eye Foundation, Los Angeles, Calif., pp. 1–9, Nov. 10–14, 1980.
Jorg H. Kormeich, "Indication, Techniques and Complications of Myopic Keratomileusis," *Int. Ph. Clinics*, 23, No. 3, pp. 80–81, Fall 1983.
José I. Barraquer et al., *Symposium on Medical and Surgical Diseases of the Cornea*, The C. V. Mosby Company (1980) pp. 428–479.

*Primary Examiner*—Gene Mancene
*Assistant Examiner*—C. W. Shedd
*Attorney, Agent, or Firm*—Nilsson, Robbins, Dalgarn, Berliner, Carson & Wurst

[57] ABSTRACT

A method for freezing corneal tissue prior to cryorefractive surgery, including the controlled rate freezing of the tissue at a rate of less than seven degrees centigrade per minute.

5 Claims, 1 Drawing Figure

CONTROLLED RATE FREEZING FOR CRYOREFRACTIVE SURGERY

The U.S. Government has rights in this invention under National Eye Institute Grant EY 04609.

FIELD OF THE INVENTION

This invention relates most generally to the fields of biology and medicine, and more particularly to the fields of ophthamology and cryorefractive surgery.

BACKGROUND AND SUMMARY OF THE INVENTION

Optical defects such as myopia, hyperopia, astigmatism and aphakia represent the most common abnormalities of the human eye. The cryorefractive surgical procedures of keratomileusis, keratophakia and epikeratophakia involve the lathing of a patient's cornea, or a donor cornea, to alter the shape and refractive power of the anterior surface of the cornea in order to correct these optical defects. Based on the cornea's preoperative refractive error, corneal tissue is placed on a lathe and frozen, and using computer-directed lathe settings the tissue is resected in a controlled fashion so as to create a lenticule that can be sewn onto or into the patient's cornea to alter the focusing system of the eye.

The cornea consists of several layers: the epithelium (five or six layers of cells which comprise the outer surface of the cornea); a basement membrane from 10 to 30 microns thick directly beneath the epithelial cells; Bowman's membrane (a sheet of acellular transparent tissue below the basement membrane, about 12 microns thick and made up of uniform fibrils of collagenous material; the stroma, further described herein, which is found beyond the Bowman's membrane; Descemet's membrane, a structureless membrane about 10 microns thick which bounds the inner surface of the stroma; and the endothelium, a single layer of cells lining Descemet's membrane which forms the inner surface of the cornea next to the aqueous humor.

The corneal stroma forms the bulk of the cornea. It is a differentiated connective tissue containing 75 to 80% water, and otherwise composed essentially of collagen (a glycoprotein) and glycosaminoglycans (proteoglycans, which are also referred to as mucopolysaccharides). Collagen is a protein having a basic unit molecular weight of about 60 kilodaltons and forms corneal fibrils which constitute the framework of the corneal stroma. Corneal collagen has a high glycine, proline and hydroxyproline content like collagen from other sources.

The glycosaminoglycans are localized in the interfibrillar space and are thought to be charged proteins which, together with the interfibrillar collagen of opposite charge, maintain the proper matrix of fibrils in the cornea. For example, in certain systemic diseases of glycosamino metabolism there is clouding of the cornea, and these glycoproteins are thus thought to be involved in the maintenance of the level of hydration and transparency of the cornea.

The stroma also contains cells (keratocytes) which are responsible for the synthesis of corneal collagen and glycosaminoglycans and thus, in turn, for the maintenance of the clarity of the cornea.

Corneal transparency is explained by the lattice structure formed by the corneal collagen fibrils, which are arranged so that scattering of light is eliminated by mutual interference. As long as the fibrils are regularly arranged in a lattice and separated by less than a wavelength of light, the cornea is transparent. If the arrangement of the fibers is distorted, destructive interference no longer occurs and the cornea becomes hazy.

Although the corneal cryo-surgical techniques have been of substantial benefit in the treatment of myopia, hyperopia, astigmatism and other corneal dysfunction, in all forms of refractive cryolathe surgery there is a substantial delay in visual recovery. Specifically, it is not uncommon following these procedures for a patient to be unable to achieve optimal corrected visual acuity of better than 20/30 until approximately one year following the surgery.

The standard protocol for cryorefractive surgery employs a Barraquer cryolathe, manufactured by Steinway Instrument Co., Inc. of San Diego, Calif. The Barraquer cryolathe freezes tissue by the expansion of carbon dioxide gas, and requires a carbon dioxide pressure of 800 p.s.i., thus producing a freezing rate of about thirty-three degrees centigrade per minute. Prior to this invention, maximum freezing rate was thought necessary for cryorefractive lathing so that the excision, lathing and reimplantation could be accomplished as soon as possible.

According to the present invention, a method for the controlled rate freezing in cryorefractive surgery is provided whereby corneal sections are frozen at a rate of less than about seven degrees per minute to produce substantial improvements in the corneal clarity during post-operative recovery. A freezing rate of less than five degrees/minute is preferred.

All temperatures herein are expressed in degrees centigrade.

DETAILED DESCRIPTION

Figure 1:
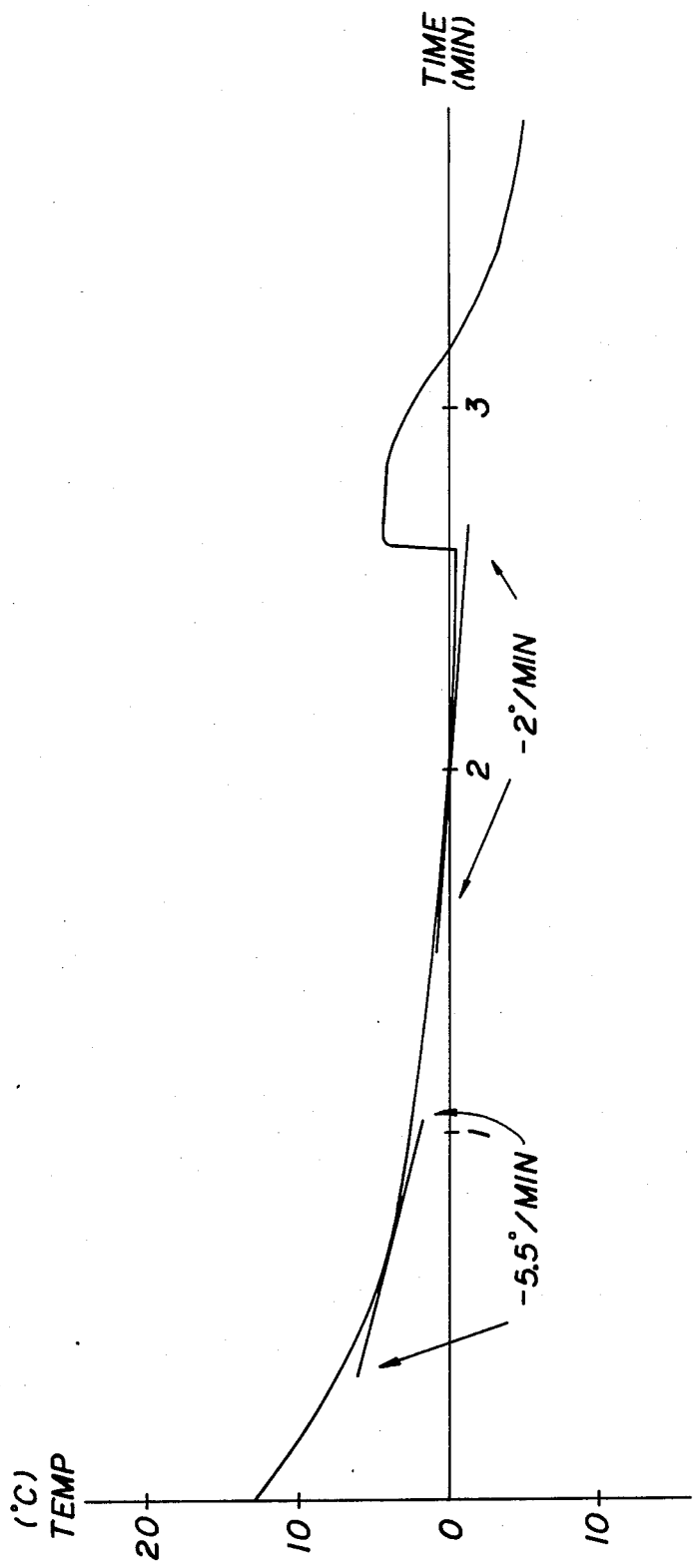
FIG. 1 is a graph of the cooling rate of corneal tissue on a Barraquer cryolathe at a carbon dioxide pressure of 450 p.s.i..

As set forth above, one of the major drawbacks of cryorefractive surgery is the delay in the postoperative recovery of corneal clarity. While I do not wish to be bound by any particular theory, it is hypothesized that this delay is due to the disruption of the collagen matrix or lattice within the stroma and the death of graft keratocytes caused by the freezing process, and the need for subsequent fibril realignment and repopulation by host keratocytes to restore corneal clarity. As described in the examples, the controlled-rate freezing process of the invention maintains clarity in corneal tissue as assessed by histologic methods and by collagenase digestion.

The Barraquer cryolathe consists of a modified Levin contact lens lathe cooled by a compressed carbon dioxide refrigeration system. In the following examples, the cooling system was modified by placing a high pressure single-stage carbon dioxide regulator between the gas cylinders and the cryolathe system, and by varying the delivery pressure the cooling rate of the cryolathe could be controlled. Temperature of the corneal buttons was measured using a calibrated microthermocouple applied to the central external corneal surface, and recorded as a function of time using a linear amplifier and single channel chart recorder.

Rabbit corneal buttons were excised using a 7 trephine, then immersed for one minute in a cryoprotectant solution. The lathe head was precooled to −12° C. immediately prior to each rate determination to allow uniform cooling curves. Each corneal button was placed on a cupped polymethylmethacrylate or Oelein lathing base of 1.5 mm central thickness, mounted on lathe head immediately after precooling, and cooled at the standard delivery pressure of 800 p.s.i., or at lower pressures of 625, 450 or 375 p.s.i. Due to the fact that the cooling curves were non-linear, the freezing rate was defined as the cooling rate of the cornea over the fairly linear interval between 20 and 10 seconds prior to visible crystallization.

The standard Barraquer protocol pressure of 800 p.s.i. produced a freezing rate of about thirtythree degrees/minute (±20%) to about −10° to −20° C.. Cooling to less than −40° C. is unnecessary and of no advantage as lathing is not improved, and substantial cooling cost and equipment are required. Decreasing the inlet pressure to 625 p.s.i. resulted in a freezing rate of twelve degrees per minute (±20%); and an inlet pressure of 450 p.s.i. produced freezing rates of from one-half to four and one-half degrees/minute, which averaged about two degrees/minute. This freezing rate was determined, as set forth above, between 20 and 10 seconds prior to visible crystallization. At both twelve and two degrees/minute, cooling to about −10° C. resulted. At 375 p.s.i., a slow asymptotic decrease in temperature to approximately +5° C. was noted, but no freezing of tissue occurred.

Following lathing, the corneal buttons were thawed at body temperature and tested as described.

EXAMPLE ONE

Keratocyte Viability Assay

The effects of different freezing rates on keratocyte survival in corneal buttons was determined using a modified collagenase digestion assay to measure cell viability. Each corneal button was placed on a 15 mL plastic conical tube containing 2 mL of 0.1% Type IV collagenase in Dulbecco's Modified Eagle's Medium with 100 units per mL penicillin, 100 units per ml streptomycin, and 2 mM L-glutamine at 330 mOsm and pH 7.4. Each cornea was incubated in this solution in a humidified 5% carbon dioxide atmosphere at 35° C. for eighteen hours, gently vortexed for thirty seconds, and thereafter centrifuged at 850 XG and decanted. The pellet was resuspended in 0.5 mL of the culture medium, to which 50 µL of 0.4% trypan blue was added. Stained non-viable and unstained viable cells were counted on a hemocytometer slide over a total volume of 0.5 µL, and the results extrapolated to estimate the number of viable cells per corneal button. Since non-viable cells could degenerate completely during incubation and might not be visible on staining, the non-viable counts could not be similarly extrapolated.

A population of sixteen rabbits was divided into two equal groups according to the pressure setting to freeze the experimental corneas. Each animal was sedated with a combined intramuscular injection of 10 mg/kg xylazine hydrochloride and 50 mg/kg ketamine hydrochloride, then sacrificed with a lethal dose of intravenous pentobarbital. One randomly selected cornea of each rabbit was designated the experimental cornea. The epithelium of this cornea was removed by gentle scraping with a No. 10 beaver blade and a 7 mm corneal button was excised using a disposable trephine. The endothelium was removed with a cotton swab and the button was immersed in a cryoprotectant solution, then blotted dry. The button was placed on a cupped polymethylmethacrylyate lathing base and frozen one minute following visible crystallization. The cornea was then thawed in McCarey-Kaufman medium at 35° C. for thirty seconds. The matching cornea from each rabbit was excised and treated in a similar manner but not frozen, and thus functioned as a matching non-frozen control. Each cornea was digested using collagenase and the viable cells were counted. The percent cell survival, defined as the ratio of viable cells in the frozen cornea compared to the paired non-frozen control cornea, was calculated for each rabbit.

In the non-frozen control corneas, a mean of $25.9 \times 10^4$ (SD $5.3 \times 10^4$), viable cells per 7 mm diameter button were recovered. At a freezing rate of thirty-three degrees/minute, a mean $\times 6.2 \times 10^4$ viable cells per button were recovered, with a mean cell survival of 25.1% (SD 11.1%). From the corneas frozen at −2° C./minute, a mean of $17.2 10^4$ viable cells per button were recovered, with a mean cell survival of 66.7% (SD 9.1%). This difference in cell survival between the rapid-frozen and the slow-frozen groups was highly significant ($t=8.203$, $p= >0.005$).

EXAMPLE TWO

Surgical Model

Using the techniques described in Schanzlin et al., "*Cryolathe Corneal Injury*", Cornea 2: 57 1983, the teachings of which are hereby incorporated by reference, twelve rabbits underwent monocular lamellar keratoplasty using autologous corneal grafts. This population was divided into three equal groups: the first group received fresh non-frozen grafts, the second group received grafts frozen at two degrees/minute rate, and the last group received grafts frozen at the rate of thirty-three degrees/minute. Each animal was sedated as described in Example One, and a lamellar corneal button was removed using a Barraquer microkeratome. Each graft was immersed for one minute in a cryopreservative, frozen according to group, and thawed in M-K medium at 35° C. for thirty seconds. The graft was replaced on the eye end secured with a running 10-0 nylon suture. The animals were examined and ultrasonic pachymetry was performed immediately pre- and postoperatively, as well as at three and seven days after surgery.

The lamellar keratoplasty confirmed the difference between control-rate, slow-frozen and the standard rapid-frozen tissue. In all cases the controlrate frozen tissue behaved much like non-frozen tissue during the grafting procedure.

Slit lamp examination of these rabbits at three and seven days revealed marked haziness and thickening of each of the rapid-frozen grafts, with much irregularity of the graft-host interface.

In contrast, the slow-frozen grafts were clearer and thinner, with less interface disruption and were virtually indistinguishable from the non-frozen control grafts.

Immediately after surgery all three groups had similar increases in mean corneal thickness. In the non-frozen and slow-frozen groups the mean corneal thickness returned almost to preoperative values by the third postoperative day, whereas in the rapid-frozen group the corneas remained markedly thickened through the seventh postoperative day.

The histologic keratocyte survivals for the two types of frozen grafts parallel the keratocyte survivals measured using collagenase digestion. The cell counts at seven days increased from the counts at three days due to keratocyte repopulation from the host tissue; however, the keratocyte survivals in the non-frozen and slow-frozen groups remained significantly higher than that of the rapid-frozen groups.

Ultrastructural examination of these corneas revealed several additional differences between rapidfrozen and controlled-rate slow-frozen grafts. Within the rapid-frozen grafts, the few remaining keratocytes appeared extensively damaged, whereas in the slow-frozen grafts the keratocytes, while reduced in number compared to the non-frozen controls, exhibited generally normal intracellular morphology. Marked disorganization was seen at the graft interface in rapid-frozen corneas, compared to the relatively normal stromal pattern seen at the interface in slow-frozen and non-frozen corneas. Changes were also noted outside the graft tissue, particularly in the endothelial layer. Electron-dense excresences on Descemet's membrane, as well as endothelial cell vacuolization and degeneration, were present in all rapid-frozen corneas but were absent in the controlled-rate slow-frozen and non-frozen corneas.

EXAMPLE THREE

Epikeratophakia

Epikeratophakia is a procedure in which a lenticle of donor corneal tissue is grafted to the surface of the patient's cornea. Recently, it has become possible to lyophilize epikeratophakia lenticles following lathing, making storage and transportation much easier. However, the problems in post-operative visual acuity which have been described above are a particular problem in lyophilized epikeratophakia grafts.

Epikeratophakia was performed on four rabbits using both lyophilized and slow-frozen lathed lenticles. All grafts were obtained from fresh donor rabbit corneas; the lyophilized lenticles were rapid-frozen, lathed and lyophilized, while the slow-frozen lenticles were slow-frozen at the two degree/minute rate and lathed on the Barraquer Cryolathe. All lenticles were lathed to plano power, and were grafted onto the host rabbits using standard epikeratophakia techniques. The eyes were photographed at three and seven days post-operatively.

Slit lamp photographs clearly demonstrated that the lyophilized epikeratophakia grafts were much thicker, and hazier than the corresponding slow-frozen grafts at three days. This difference was still readily apparent at seven days.

EXAMPLE FOUR

Primate Epikeratophakia

Epikeratophakia was performed on a baboon (papio sp.) to investigate the results of controlled-rate freezing with respect to primates. A human donor cornea unsuitable for human use was obtained from an eye bank and frozen at a rate of the two degree/minute rate to about $-10°$ C. The frozen corneal button was then lathed to $+10$ diopter power, and grafted onto the baboon eye using standard epikeratophakia techniques.

In a normal human epikeratophakia procedure, corneal swelling and haziness lasts for several weeks following the implantation. Three days following the grafting procedure described in this Example, the cornea was clear and swelling was minimum.

While the examples detailed herein employ the standard cryoprotectant solution known as KM-26 (0.25% kiton green, 8% glycerol and 4% dimethylsulfoxide), it has been found that solutions with balanced ionic strength offer substantial benefits in keratocyte survival. A preferred solution contains 10% glycerine and 0.25% light-green yellowish dye which is adjusted to 400 mOsm ionic strength with sodium chloride (pH 4.25).

About two hundred separate corneal buttons have been frozen as described herein, of which about thirty were grafted and showed substantial improvement in clarity following cryorefractive surgery. The remaining corneal buttons were examined as described in Example One and showed a similar increase in keratocyte survival.

A representative curve of the cooling of the corneal tissue at 450 p.s.i. is shown in FIG. 1. As described, the cooling rates were recorded using a chart recorder, and the curve produced was not strictly linear. The rates of freezing referred to herein were thus measured over the fairly linear range between twenty and ten seconds prior to crystallization. However, the rate at earlier periods was somewhat higher, and thus the overall cooling rate at 450 p.s.i. is seen to have varied from about twenty-four to about one-half degree C. per minute. The standard deviation of the rates shown in FIG. 1 is about two degrees.

The critical portion of the cooling curve is that portion from a temperature of about $+4°$ C. down to the lathing temperature of the Barraquer cryolathe, about $-10$ C.. That portion of the curve of FIG. 1 seen involves a cooling rate which varies from about five degrees per minute (with a S.D. of two degrees, i.e., up to seven degrees/minute) down to what is thought to be the minimum operable freezing rate, one half degree per minute. Other data specifically show beneficial results from cooling rates in the range of from seven to one-half degrees/minute over the critical range of temperatures less than $+4°$ Centigrade.

From the foregoing description, one skilled in the art can readily ascertain the essential characteristics of the invention and, without departing from the spirit and scope thereof, can adapt the invention to various usages and conditions. Changes in form and the substitution of equivalents are contemplated as circumstances may suggest or render expedient; and although specific terms have been employed herein, they are intended in a descriptive sense and not for purposes of limitation, the purview of the invention being delineated in the following claims.

What is claimed is:

1. In a method for refractive keratoplasty which includes freezing and lathing a corneal portion to modify the surface curvature thereof, the improvement comprising the steps of cooling the corneal portion at a rate of less than about 7° C. per minute over a temperature range below $+4°$ C. to a temperature above $-40°$ C. to freeze the corneal portion, and lathing the surface of the frozen corneal portion to a predetermined curvature.

2. The method of claim 1 wherein the cooling proceeds at a rate of from about $\frac{1}{2}$ to $4\frac{1}{2}°$ C. per minute.

3. The method of claims 1 or 2 wherein the corneal portion is cooled to a temperature of from $-10°$ C. to $-$ ° C.

4. A method for performing cryorefractive surgery on the cornea of a patient, comprising:
   obtaining a corneal portion;

cooling the corneal portion, over a temperature range of below 4° C., at a rate of less than 7° C. per minute until the corneal portion is frozen;

lathing the surface of the frozen corneal portion to a predetermined curvature;

thawing the lathed corneal portion to about room temperature; and grafting the lathed corneal portion to the cornea of the patient.

5. The method of claim 4 wherein the cooling proceeds at a rate of from about ½ to 5° C. per minute to a temperature of −10°−20° C.

* * * * *

UNITED STATES PATENT AND TRADEMARK OFFICE
CERTIFICATE OF CORRECTION

PATENT NO. : 4,664,110
DATED : May 12, 1987
INVENTOR(S) : DAVID J. SCHANZLIN

It is certified that error appears in the above—identified patent and that said Letters Patent is hereby corrected as shown below:

Column 2, line 67, after "7", insert --mm--;

Column 3, line 5, after "on", insert --the--;

Column 3, line 14, delete "thirtythree" and insert --thirty-three--;

Column 4, line 16, after "mean", delete the first "x" and insert --of--;

Column 4, line 19, after "17.2", insert -- x --;

Column 4, line 51, delete "controlrate" and insert --control-rate--;

Column 5, line 10, delete "rapidfrozen" and insert --rapid-frozen--;

In claim 1, line 2, delete "latching" and insert --lathing--;

In claim 3, line 3, between "-" and "°C", insert --20--; and

UNITED STATES PATENT AND TRADEMARK OFFICE
CERTIFICATE OF CORRECTION

PATENT NO. : 4,664,110

DATED : May 12, 1987

INVENTOR(S) : DAVID J. SCHANZLIN

It is certified that error appears in the above-identified patent and that said Letters Patent is hereby corrected as shown below:

In claim 5, line 3, between "-10°" and "-20°C", insert -- to --.

Signed and Sealed this

Eighteenth Day of August, 1987

Attest:

DONALD J. QUIGG

Attesting Officer

Commissioner of Patents and Trademarks